United States Patent [19]

Lord

[11] 4,427,976
[45] Jan. 24, 1984

[54] MOISTURE SENSOR

[75] Inventor: Peter M. Lord, Porthcawl, Wales

[73] Assignee: Coal Industry (Patents) Limited, London, England

[21] Appl. No.: 68,806

[22] Filed: Aug. 22, 1979

[30] Foreign Application Priority Data

Aug. 25, 1978 [GB] United Kingdom ............ 34715/78

[51] Int. Cl.³ .......................................... G08B 21/00
[52] U.S. Cl. ...................................... 340/604; 73/73;
73/336.5; 200/61.04; 200/61.05
[58] Field of Search ............... 340/602, 604, 605;
73/73, 336.5; 324/65 R; 200/61.04, 61.05, 61.06

[56] References Cited

U.S. PATENT DOCUMENTS

| 2,360,434 | 10/1944 | Manning | 340/605 |
| 2,681,571 | 6/1954 | Becker | 73/73 X |
| 2,759,175 | 8/1956 | Spalding | 200/61.04 X |
| 2,768,370 | 10/1956 | Maninger | 340/632 X |
| 3,253,315 | 5/1966 | Elcken | 73/73 X |
| 3,332,279 | 7/1967 | Tompos et al. | 73/73 |
| 3,721,970 | 3/1973 | Niemoth | 340/605 |

FOREIGN PATENT DOCUMENTS 433172 8/1935 United Kingdom .
822566 8/1959 United Kingdom .

Primary Examiner—Gerald L. Brigance
Assistant Examiner—Daniel Myer
Attorney, Agent, or Firm—James Creighton Wray

[57] ABSTRACT

This invention relates to a device for sensing moisture on a metal surface such as a brake path. Since the presence of moisture on a brake path causes inefficient working of the brake, it is necessary to test for moisture. Originally this was done by hand. The present invention provides a device which can test for moisture automatically. The device comprises a pair of contacts urged against an electrically conducting surface. One contact is covered by a strip of material, for instance paper, which is an insulator when dry and a conductor when moist. If moisture is present an electrical circuit comprising the surface, the moist material and the two contacts is completed activating an alarm. The material may be salt impregnated and the contacts may be moveable over the surface. The device is for use in testing for moisture on the braking surface of colliery winding installations.

12 Claims, 4 Drawing Figures

MOISTURE SENSOR

This invention relates to a device for sensing moisture on an electrically conducting surface, and particularly, but not exclusively, relates to such a device for use on braking surfaces in colliery winding installations.

According to the present invention there is provided a device for sensing moisture on an electrically conductive surface, the device comprising a contact and a piece of material which is electrically insulating when dry and electrically conductive when moist, the contact, in use, being urged towards the surface, locating the material between it and the surface, whereby, if the surface is moist, the material is moistened and becomes electrically conducting, thereby completing an electrical circuit comprising the contact, the material and the surface.

In a colliery winding system for raising and lowering men and materials in a mine shaft, winding and braking are normally accomplished by use of electric motors acting either as motors, for winding, or as generators, for braking. However the braking is always supplemented, and in emergencies is supplied solely, by mechanical friction brakes acting on the winder drums. The brakes may be either disc or caliper type brakes.

The efficiency of the action of these brakes is dependent on the coefficient of friction between the brake pads and the braking path. The braking path may be either the disc surface or a surface of the winder drum on which the caliper brakes act. The coefficient of friction, and therefore the efficiency of the brakes, is reduced considerably by the presence of moisture of the braking path. It is therefore the practice in some winding installations to test the brake paths for moisture prior to winding or braking. Originally this was carried out manually, which was time consuming and wasteful of manpower. There was therefore a need for a device which could be used remotely and quickly to sense any moisture on the braking paths. The device according to the present invention was developed to fill this need.

Preferably the device includes a further contact which, in use, is urged into direct electrical contact with the surface. Conveniently the two contacts are located in a single head, and are electrically insulated from one another in the head. The head may be urged against the surface by any suitable means, for instance a leaf spring. Preferably also one or the other of the contacts is independently spring loaded so that it is possible to ensure that even on an irregular surface both contacts are capable of contacting the surface. Advantageously the further contact is spring loaded.

Preferably the two contacts are joined into a circuit which when completed sets off an audible or visible alarm. The alarm may be located on the device or may be remote therefrom, for instance in a control room. Alternatively the circuit when completed may generate a signal which is fed into a computer-mediated control system.

The piece of material may be supplied as individual pieces which are manually clamped over the first contact before each sensing operation. However, prefereably the material is in the form of an elongate strip which is movable in discrete steps in one direction only at the end of each sensing operation so that a fresh part of the strip is located to be trapped between the first contact and the surface during each sensing operation. Advantageously the strip of material is mounted on a reel and is reeled off that reel onto a second reel in discrete steps. The reeling may be achieved manually but is preferably achieved automatically for instance by use of an electric motor or an automatic mechanical mechanism.

Preferably the head is adapted to be drawn across the surface so as to be able to sense any moisture on a strip of the surface, rather than just on a single small area. This movement may be achieved by use of an electric motor and any conventional type of rotary to linear motion conversion system. Advantageously the head at the end of its stroke across the surface is lifted off the surface so that it is, when not being used, in a position away from the surface, this position also being its starting position. This may be achieved for instance by use of a cam contacting an abutment. Conveniently, if the strip is to be reeled, there is provided a ratchet on the take-in reel which is wound on by a pawl mounted on a lever which is adapted to abut a stop towards the end of the stroke of the head. As the head completes its stroke, the stop causes the lever to pivot and, with the pawl engaged on the ratchet, causing the reel to be wound round a discrete amount.

The material may comprise any water absorbent material and should be strong enough to retain its intergrity when wet and if necessary to withstand being drawn across a rough surface. Examples of material which may be used are blotting paper, filter paper, cotton, linen, nylon or other synthetic materials. Preferably the material is impregnated with a salt, such as common salt, to increase the conductivity of the moist material. Care should be taken to ensure that the material is not so heavily impregnated that it is conductive when dry, nor that it could cause corrosion of the surface. It has been found that cotton impregnated with a saturated solution of common salt satisfies these requirements.

Preferably the device is remotely operable and advantageously is battery operable. Therefore all movement is preferably caused by use of a single electric motor and necessary levers, cams etc.

The device according to the present invention may be made very sensitive by varying the degree of impregnation of the material, the distance the head is drawn across the surface, or the size of the piece of material in contact with the surface. These operating parameters may be determined in relation to the use to which the device is to be put.

It is envisaged that the device of the present invention will be of especial use in colliery winding installations. Advantageously the device will be remotely operated and will be programmed to carry out a sensing operation either at regular time intervals or before a winding operation begins.

However the device may also be used for instance on other braking surfaces or on remote electrical installations such as in power stations or in computer systems where the presence of moisture may cause at the least inefficient operation and at worst catastrophic short circuiting.

The device according to the present invention will now be described, by way of example only, with reference to the accompanying drawings, in which.

Figure 1:
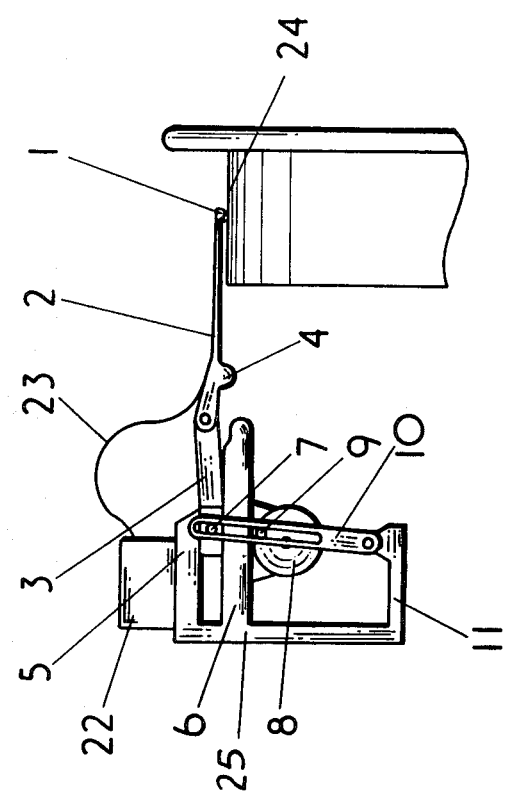
FIG. 1 shows a side view of a device according to the invention.

Referring now to FIG. 1, the device comprises a head 1 connected to an arm 2. The end of the arm 2 remote from the head 1 is pivotally connected to a member 3 which is slidably movable along a path defined by two struts 5 and 6, substantially parallel to the arm 2. Near the end of the arm 2 remote from the head 1 is a cam 4 which is adapted to abut a curved abutment on the end of the second strut 6. A box 22 containing electric control circuitry and a sensing circuit is fixed onto the top of the first strut 5, and a leaf spring 23 is fixed between the box 22 and the arm 2 so that, in use, the head 1 is urged towards a surface 24 comprising a brake drum in a colliery winding installation on which there may be moisture.

A pin 7 is fixed to the member 3 at right angles thereto towards its end remote from the arm 2. An electric motor 8 is fixed onto the bottom of the second strut 6, and has rotatably mounted on it an eccentric pin 9 which extends parallel to the pin 7. A slotted lever 10 is pivotally mounted on a third strut 11 below the motor 8, the slot of the lever 10 fitting over the pins 7 and 9. The struts 5, 6 and 11 are held together on a frame 25.

Figure 2:
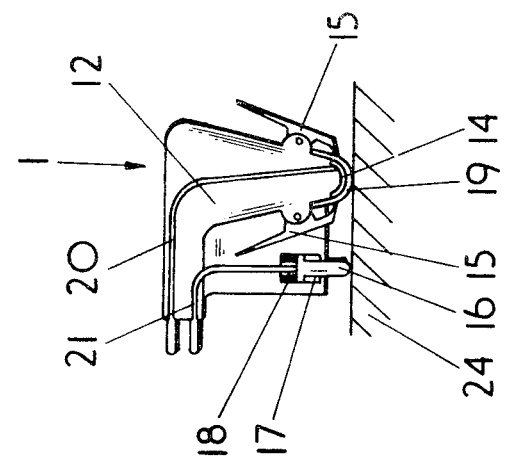
FIG. 2 shows a side view of a detail of FIG. 1.

The head 1 is shown in more detail in FIG. 2, to which reference is now also made. The head 1 comprises a tapered body 12, having on its tapered end a contact plate 14 made of stainless steel. The tapered end is below the rest of the body as seen in FIGS. 1 and 2. A clamp 15 is mounted on the body 12 and a second contact 16 is fitted into a recess 17 in the body 12. The second contact 16 is biased downwardly, as seen in FIG. 2 by a coil spring 18. The two contacts 14 and 16 are connected to the sensing circuit by wires 20 and 21 respectively. In use, the clamp 15 is used to retain a piece of blotting paper 19 over the contact plate 14. The blotting paper is impregnated with a saturated solution of common salt to increase its conductivity when moist.

Figure 3:
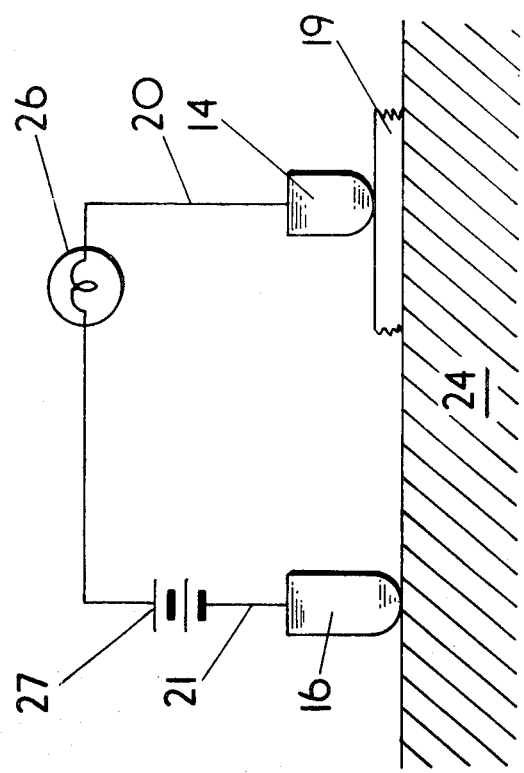
FIG. 3 shows a circuit diagram for the device of FIG. 1.

The sensing circuit is shown in FIG. 3, to which reference is now made, and comprises the contact plate 14, the blotting paper 19, the surface 24, which in this case is a winder braking path, the second contact 16, a lamp 26 and a battery 27. When the paper 19 is dry the lamp 26 remains unlit, but will become lit if the paper becomes sufficiently moist to become conducting. The lamp 26 may be replaced by an audible warning, such as a bell, or the lamp 26 may be removed and the circuit be adapted to feed a signal to a computer-mediated control system.

The device is used in the following manner to carry out an operation to sense any moisture on the brake path 24. A fresh piece of salt—impregnated blotting paper 19 is clamped over the contact plate 14 and the head 1 is moved from its starting position to the position shown in FIG. 1. This may be achieved by use of the electric motor 8 or manually. The motor 8 is then activated and as it turns the circular movement of the second pin 9 is translated into a lateral movement of the member 3 and arm 2 by the action of the lever 10 and the first pin 7 in known manner. The head 1, which is urged against the surface 24 by the action of the leaf spring 23, is therefore drawn across the surface 24 from right to left as seen in FIG. 1. The action of the spring 23 ensures that the paper 19 is always kept in contact with the surface 24 because of the pressure exerted on it by the contact plate 14. The second contact 16 is kept in direct electrical contact with the surface 24 by the action of the spring 18.

If there is any moisture on the surface 24, the paper 19 will be moistened and become conductive. The circuit will therefore be completed, causing the lamp 26 to light, the alarm to sound, or the computer to take appropriate action.

As the member 3 approaches the frame 25 the cam 4 will abut the shaped end of the strut 6, causing the arm 2 to pivot and bringing the head 1 out of contact with the surface 24, against the bias of the spring 23 and into its starting and rest position. The motor 8 is stopped at the end of its movement towards the frame 25, completing a sensing operation. The head is left in this position until it is to be used again in a sensing operation. The paper 19 may then be replaced and the motor activated to move the head 1 to the position shown in FIG. 1, whereupon the device is ready to carry out another sensing operation. This simple operation quickly and easily enables a determination of whether or not there is any moisture on a braking path to be made.

Figure 4:
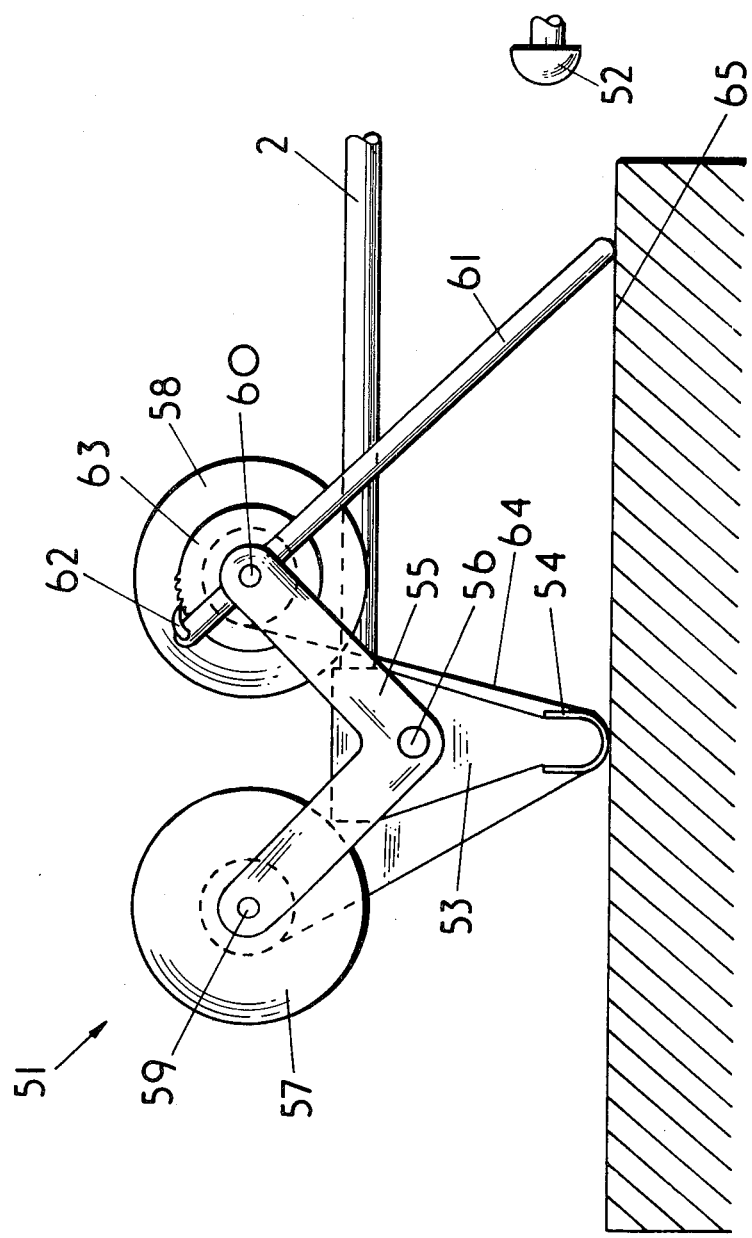
FIG. 4 shows a side view of an improved head for use in the device of FIG. 1.

The device in described in FIG. 1 may be improved by replacing the head 1 with the head 51 shown in FIG. 4, to which reference is now made. In addition a stop 52 needs to be attached to the frame 25 or one of the struts 5, 6 and 11 for reasons which will be explained later.

The improved head 51 comprises a tapered body 53 attached to the arm 2. A contact plate 54 made of stainless steel is attached to the tapered end of the body 53, which is at the bottom as seen in FIG. 4. A V-shaped member 55 is fixed with its apex downwards as seen in FIG. 4 by a pin 56 through it apex to the body 53. A reel 57 or 58 is rotatably mounted on a shaft 59 or 60 respectively on each end of the V-shaped member 55. A lever 61 having a pawl 62 rotatably mounted on its end is rotatably mounted on the shaft 60. The pawl 62 is adapted to engage with a ratchet 63 fixed on one side of the reel 58. An elongate strip of cotton 64 impregnated with a saturated solution of common salt is wound on the reels 57 and 58 and passes over the contact plate 54. In use, the cotton strip is reeled off reel 57 and onto reel 58. A second contact (not shown) is fitted in the body and spring biased in a similar fashion to the second contact in FIG. 1. The two contacts are joined into an electric circuit of the same type as that shown in FIG. 3.

The stop 52 is positioned such that in use, as the head is moved towards the struts (not shown but similar to those in FIG. 1), when the cam comes into abutment with the shaped end of the second strut, the lever 61 abuts the stop 52. Thus as the head 51 continues its movement, the lever 61 is caused to rotate about the shaft 60, causing the pawl 62 which is engaged with the ratchet 63 to rotate the reel 58 and thereby reel in a portion of the strip of cotton 64. In this way after every traverse of the head across brake path 65, a new discrete piece of the material is moved into position for a fresh determination. Since the pawl 62 and ratchet 63 mechanism can only act to rotate the reel 58 in one sense the material 64 is not reeled back as the head 51 is moved back to its starting position.

The operation of the device including the improved head 51 is exactly the same as that for the device of FIG. 1 except that the necessity for manually changing the strip of material is obviated Thus a device including the head of FIG. 4 is operable remotely and automatically until the reel of cotton is used up.

The device of the present invention is simple, can be remotely operated, is sensitive, and can be adapted to produce any desired sort of output. It is therefore useful in colliery winding installations for the remote effective sensing of moisture on brake paths.

I claim:

1. A device for sensing moisture on an electrically conductive surface comprising a supporting member positioned above the surface, first and second electrical contacts mounted on the supporting member and electrically insulated from one another, material which is electrically conductive when moist and electrically insulating when dry, material location means mounted on the supporting member for positioning the material between the first contact and the surface, bias means for biasing the supporting member toward the surface so that the piece of material is trapped between the first contact and the surface and the second contact is brought into direct electrical contact with the surface, and electrical circuit means for applying voltage across the two contacts, said electrical circuit means comprising means for indicating when a current is flowing between the two contacts, whereby if the surface is moist, the piece of material is moistened and becomes electrically conductive, and the electrical circuit indicates that a current is flowing between the contacts, thereby indicating the presence of moisture on the surface.

2. A device according to claim 1 wherein the supporting member is provided with second bias means for biasing one of the contacts toward the surface independently of the other contact.

3. A device according to claim 1 wherein the supporting member is provided with means for moving the supporting member across the surface.

4. A device according to claim 3 wherein the moving means is provided with means for raising the supporting member upwardly from the surface at the end of a movement of the supporting member across the surface.

5. A device according to claim 4 wherein the raising means comprises a guide, an element pivotally connected to the supporting member and mounted for reciprocating movement on said guide, and an abutment positioned on said guide to engage a projection formed on the supporting member at the end of said movement of the supporting member across the surface to urge the supporting member to pivot about the element.

6. A device according to claim 1 wherein the material is in the form of an elongated strip which is wound onto a pair of reels, the supporting member being provided with means for reeling the material from one reel to the other.

7. A device according to claim 6 wherein one of the reels is provided with a ratchet, and the reeling means is provided with a lever having first and second ends and being pivotally mounted between said ends, a pawl on said ratchet, and an abutment positioned adjacent to the surface, the abutment being moved into engagement with the second end of the lever near said end of said movement of said supporting member, continued movement of said supporting member toward said end pivoting the lever and imparting movement to said pawl which is communicated through the ratchet to the reel.

8. A device according to claim 6 wherein the supporting member is provided with means for moving the supporting member across the surface.

9. A device according to claim 8 wherein the moving means comprises a guide mounting the supporting member for slideable movement, a pivotally mounted lever engaging the supporting member, and means for pivoting the lever, said pivoting of said lever imparting slide movement to the supporting member.

10. A device according to claim 9 wherein the pivoting means comprises a pin received within a longitudinal slot formed in the lever, and means connected to the pin for moving the pin about a circular path, said circular movement imparting pivotal movement to said lever.

11. A device according to claim 9 wherein the supporting member is provided with an outwardly extending pin received within a slot formed in the lever.

12. A device according to claim 1 wherein the supporting member is supported apart from the electrically conductive surface.

* * * * *